United States Patent
Bowen et al.

(10) Patent No.: US 7,442,822 B2
(45) Date of Patent: Oct. 28, 2008

(54) STABILIZATION OF NITROGEN-CONTAINING AND OXYGEN-CONTAINING ORGANOSILANES USING WEAKLY BASIC ION-EXCHANGE RESINS

(75) Inventors: Heather Regina Bowen, Vista, CA (US); Xinjian Lei, Vista, CA (US); Lee Arthur Senecal, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/514,650

(22) Filed: Sep. 1, 2006

(65) Prior Publication Data

US 2008/0058541 A1   Mar. 6, 2008

(51) Int. Cl.
*C07F 7/10* (2006.01)
(52) U.S. Cl. ...................................... 556/413
(58) Field of Classification Search ............... None
See application file for complete search history.

(56) References Cited

U.S. PATENT DOCUMENTS

| 2,834,648 | A | 5/1958 | Bailey et al. |
| 3,928,542 | A | 12/1975 | Bakey |
| 4,228,092 | A | 10/1980 | Kotzsch et al. |
| 4,368,313 | A | 1/1983 | Hayes |
| 4,709,067 | A | 11/1987 | Chu et al. |
| 4,798,889 | A | 1/1989 | Plueddemann et al. |
| 6,963,006 | B2 | 11/2005 | Tsui et al. |

FOREIGN PATENT DOCUMENTS

| EP | 0 028 524 |   | 8/1984 |
| EP | 0 206 621 |   | 11/1989 |
| EP | 0 367 492 | A | 5/1990 |

OTHER PUBLICATIONS

B.J. Aylett, et al, "The Preparation and Properties of Dimethylamino- and Diethylamino-silane," J. Chem. Soc. (A), 1967, pp. 652-655.
David G. Anderson, et al, "Isopropyldisilylamine and Disilyl-t-butylamine: Preparation, Spectroscopic Properties . . . ," J. Chem. Soc. Dalton Trans., 1989, pp. 779-783.
Radhamani, K.N., et al; "A Convenient High Yield Room Temperature Synthesis of Mixed Tri(amino)silanes by Transamination of Tris(dicyclohexlyamino)silane and their Characteriisation"; Phosphorus, Sulfur and Silicon and the Related Elements; Gordon and Breach Science Publishers; Amsterdam, GB; 1993; vol. 79; pp. 65-68; XP009031036.

*Primary Examiner*—Samuel A Barts
(74) *Attorney, Agent, or Firm*—Geoffrey L. Chase

(57) ABSTRACT

A process to stabilize nitrogen-containing or oxygen-containing organosilane from acid catalyzed attack and retard the resulting decomposition is disclosed. Such organosilanes, and the nitrogen-containing organosilane in particular, with a least one Si—H or N—H group are susceptible to this type of product decomposition. Treatment with a weakly basic ion exchange media retards this decomposition by scavenging the anions or acids that are attacking the Si—H group. Dilute exposures to these anions can initiate significant decomposition and effect product stability and long-term shelf-life for semiconductor processing for the use of silicon oxide, silicon oxynitride and silicon nitride films.

15 Claims, No Drawings

STABILIZATION OF NITROGEN-CONTAINING AND OXYGEN-CONTAINING ORGANOSILANES USING WEAKLY BASIC ION-EXCHANGE RESINS

BACKGROUND OF THE INVENTION

Nitrogen-containing organosilanes such as alkylaminosilanes or dialkylaminosilanes are used as precursors for depositing, via chemical vapor deposition (CVD) or similar means, silicon nitride, silicon carbonitride, and silicon oxynitride films that can be used in semiconductor device fabrication.

The alkylaminosilanes, for example bis(tertiary-butylamino)silane (BTBAS) and dialkylaminosilanes, for example diethylaminosilane (DEAS) and di-isopropylaminosilane (DIPAS), are representative of liquid phase nitrogen-containing aminosilane chemical precursors and are employed for the chemical vapor deposition (CVD) or plasma enhanced chemical vapor deposition (PECVD) of silicon nitride, silicon oxynitride and silicon dioxide films. The deposited films obtained using BTBAS as the precursor with ammonia, for example, are free of ammonium chloride and chlorine contamination as compared to the films deposited from dichlorosilane (DCS) and ammonia via CVD. And such films can be formed at relatively low process temperatures, i.e., 500 to 600° C. Furthermore, these alkylaminosilanes or dialkylaminosilanes produce films which are substantially free, or contain very low levels, of carbon due to the fact they do not contain direct Si—C bonds.

Oxygen-containing organosilane liquids, for example diethoxymethylsilane, are used for the plasma enhanced chemical vapor deposition of silicon oxide, carbon-doped silicon oxide, porous silicon oxide. The resulting films can be employed as inter-metal layer to avoid cross-talking between copper interconnects.

The nitrogen-containing organosilanes such as BTBAS, DEAS, and DIPAS having either N—H or Si—H fragments or both and certain oxygen-containing organosilanes containing Si—H fragments often are susceptible to decomposition over time resulting in main product degradation. In some cases product decomposition can be 20-450 ppm per day and higher, thereby resulting in a significantly reduced product shelf life. Thus, there is a need in the art for an economic and expedient process to halt and stabilize nitrogen-containing and oxygen-containing organosilanes having a decomposition rate typically of at least 50 ppm/day employed for use in semiconductor applications.

The following patents are representative of the prior arts for producing nitrogen-containing organosilanes or oxygen-containing organosilanes as well as their use in depositing silicon nitride, silicon oxynitride and silicon dioxide films:

U.S. Pat. No. 6,963,006 discloses a process for producing alkylaminosilanes, and BTBAS in particular, by reacting a dichlorosilane with an alkylamine in the absence of a solvent under anhydrous conditions. A liquid comprised of an alkylaminosilane and alkylamine hydrochloride salt is formed. The alkylaminosilane is separated from the alkylamine hydrochloride salt and the alkylaminosilane purified by either atmosphere or vacuum distillation.

U.S. Pat. No. 2,834,648 discloses a process for effecting disproportionation of chlorosilanes employing amine-type catalysts. Particularly suited amines for effecting disproportionation are dialkyl and trialkyl amines.

U.S. Pat. No. 3,928,542 discloses a process for enhancing the ability of solid anion resins to effect disproportionation or redistribution of chlorosilicon hydrides, such as silicon hydrides. In the process an amino ion exchange resin is treated with HCl and the resin employed in the disproportion reaction.

EP 0028524 discloses a process for producing alkoxysilane cluster compounds of the formula:

$$RSi[SiO_4]_3[R']_{9-n}[R'']_n$$

by reacting an alkoxysilane cluster compound of the formula:

$$RSi[SiO_4]_3[R']_9$$

with an alcohol in the presence of an acidic catalyst. Representative catalysts are acidic ion-exchange resins, Lewis acids, acidic alcohols and the like.

EP 0206621 discloses a process for forming mono and dichlorosilanes by disproportionating silanes of the formula $R_1H_mSiX_{4-(1+m)}$ by contacting a silane having at least one Si—H bond of the formula:

$$R_1H_mSiX_{4-(1+m)}$$

with a neutralization adduct of a sulfonic acid-type or quaternary ammonium salt-type anion exchange resin catalyst.

U.S. Pat. No. 4,798,889 discloses a method for stabilizing unsaturated organosilicones containing specific vinylic groups in the molecule with the use of a hydroxylamine to reduce thermally induced polymerization.

U.S. Pat. No. 4,709,067 discloses a process for stabilizing methacryloxy and acryloxy organosilicon compounds with the use of a phenolic inhibitor such as MMHQ, aromatic amines or aromatic sulfur compounds in the presence of a platinum catalyst and the presence of small amounts of alcohols during the vacuum distillation.

U.S. Pat. No. 4,368,313 address stabilization of silanol hydrolysates of organosilanes to increase shelf life through the additional of a neutralizing agent containing chelatable metal ions.

U.S. Pat. No. 3,928,542 discloses the preparation of anion exchange resins with dry hydrogen chloride to enhance the ability of the resin to redistribute chlorosilanes.

Aylett and Emsley, *The Preparation and Properties of Dimethylamino and Diethylamino Silane*, J. Chem. Soc. (A) p 652-655, 1967, disclose the preparation of dimethylamino and diethylaminosilane by the reaction of silane with the respective dialkyl amine.

Anderson and Rankin, *Isopropyldisilylamine and disilyl-t-butylamine: Preparation, Spectroscopic Properties, and Molecular Structure in the Gas Phase, Determined by Electron Diffraction*, J. Chem. Soc. Dalton Trans., p 779-783 1989 disclose the synthesis of isopropyldisilylamine and disilyl-t-butylamine and provide spectroscopic comparison to the corresponding methyldisilylamine.

BRIEF SUMMARY OF THE INVENTION

This invention relates to a process for preventing decomposition of organosilanes selected from the group consisting of stable and unstable liquid phase nitrogen-containing organosilanes having at least one free Si—H or one N—H group and to certain oxygen-containing organosilanes having at least one Si—H group. They have no pendant halogen groups. The improvement in the process leading to stabilization of the organosilane product resides in contacting a liquid phase organosilane with a solid phase, weakly basic anion exchange resin for a time sufficient to remove anions as well as trace amounts of acid but insufficient to cause the organosilane product to undergo decomposition by itself. Then, the organosilane is purified via separation from the ion exchange resin, typically by filtration.

Significant advantages can be achieved by the process and these include:

an ability to reduce the rate of decomposition of organosilanes and thereby extend the shelf life thereof; and,
an ability to employ solid phase ion exchange resins which allow for the removal of contaminating anions with process efficiency.

DETAILED DESCRIPTION OF THE INVENTION

The organosilanes suited for the practice of the invention are selected from the group consisting of nitrogen-containing silanes and oxygen-containing silanes which are normally liquid at room temperature. The nitrogen-containing organosilanes susceptible to attack and destabilization over time have the general formulas:

$$(RNH)_x SiH_{4-x} \qquad 1$$

and $$(R_2N)_x SiH_{4-x} \qquad 2$$

wherein R is $C_1$-$C_{10}$ alkyl groups, cycloaliphatic, or combined into a cyclic group and x=1, 2, or 3.

Nitrogen-containing organosilanes in liquid form can be produced in various ways but typically they are formed from a reaction mixture comprised of a chlorosilane. In one form of the reaction process at least one organoamine reagent is reacted with at least one chlorosilane reagent. The organoamine reagent is present in the reaction mixture in an amount in excess of the stoichiometric amount in order to remove the chloride as an organoamine hydrochloride salt, a solid by-product.

An example of the process chemistry for producing BTBAS, which is one embodiment of the invention, resides in the reaction of tertiary butylamine (TBA) with dichlorosilane (DCS). Four moles of TBA are reacted with each mole of DCS. An amount of TBA in excess of the stoichiometric amount is used as the solvent. The BTBAS crude liquid contains two moles of by-product, tert-butylamine hydrochloride salt (TBA.HCl), which is formed for each mole of dichlorosilane (DCS) reacted. The reaction mixture may be agitated to enhance the contact between the alkylamine and the chlorosilane reagents. Agitation may be achieved, for example, by ultrasonic energy or mechanical agitation.

The reaction is conducted under anhydrous conditions to avoid hydrolysis of the chlorosilane reagent and the nitrogen-containing organosilane product. In this connection, the reactor system is thoroughly dried via heat, vacuum, or other means prior to conducting the reaction. The reaction is conducted at a temperature ranging from −10 to 50 C., preferably from 0 to 35° C. Once the reaction is complete the reactor contents are passed through a filter to substantially remove the byproduct salt from the crude liquid. Suitable filtration media are composed of a material that will not react with the crude or any of the components contained therein such as a ceramic, glass frit, or certain metals.

Product purification generally begins with the distillation removal of unreacted organoamine reagent from the nitrogen-containing organosilane. A vacuum generally is applied to assist the removal of the amine from the crude nitrogen-containing organosilane liquid. The conditions of temperature and pressure for the purification of the crude vary depending upon the purification process used.

The oxygen-containing organosilanes susceptible to attack and instability over time are characterized as being liquid phase at room temperature and having at least one Si—H group. They are represented by the formulas:

$$(R^1O)_x SiH_{4-x} \qquad 1$$

and $$(R^1O)_x R^2_y SiH_{4-x-y} \qquad 2$$

wherein $R^1$ and $R^2$ are selected from $C_1$-$C_{10}$ alkyl groups, cycloaliphatic, or combined into a cyclic group and x=1, 2, 3 in formula 1 and x+y<4 in formula 2.

One of the significant problems associated with nitrogen-containing organosilanes and the above oxygen-containing organosilanes, as mentioned previously is that of poor shelf life due to presence of trace amount of impurities. Bis(t-butylamino)silane, for example, can decompose to form mono(t-butylamino)silane (MTBAS), tris(t-butylamino)silane (TTBAS) and bis{(tert-butyl)aminosilamethyl}(tert-butyl) amine [abbreviated to S-2] liberating free t-butylamine. MTBAS and TTBAS are formed via a disproportionation reaction due to the reactivity of Si—H group which can be catalyzed by trace amount of acid as shown in equation (1). S-2 is believed to be produced by the condensation of two BTBAS molecules, which is probably associated with trace amounts of anion or cation containing impurities as shown in equation (2):

Equation 1

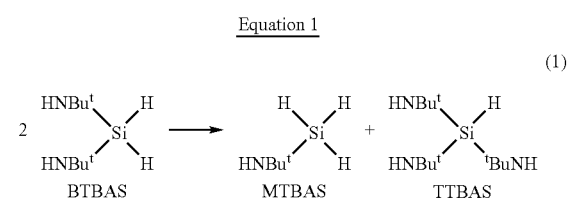

(1)

Equation 2

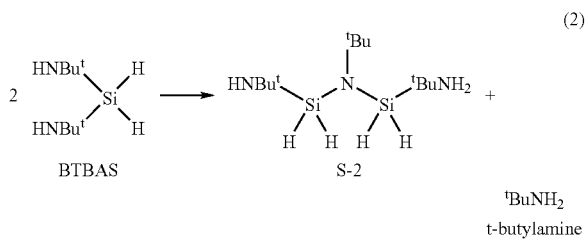

(2)

$^tBuNH_2$
t-butylamine

Diethylaminosilane can decompose to bis-diethylamino-disilane and will liberate diethylamine similar to the decomposition of BTBAS liberating t-butylamine in equation (2). Some batches of BTBAS product considered normally stable experience some decomposition, typically generating S-2 at less then 5 ppm per day at ambient temperature. On the other hand some batches of BTBAS are inherently unstable, forming S-2 at greater than 50 ppm per day. Product that decomposes at these high rates can become potentially problematic as a precursor for massive usage in the semiconductor industry.

The oxygen-containing organosilanes having at least one Si—H group also are well known to be susceptible to undergo disproportionation reactions in the similar fashion as the nitrogen-containing organosilanes as represented by equation 3:

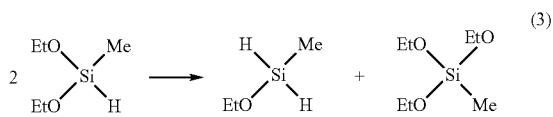

It has been found that the stability of nitrogen-containing organosilanes, and particularly batches of unstable BTBAS and DEAS, as well as certain oxygen-containing organosilanes, particularly diethoxymethylsilane (DEMS), can be improved by treatment with a weakly basic ion exchange resins. (The term "weakly basic" is one characterized by the manufacturers and refers to the environment of use.) The weakly basic ion exchange resins suitable for use in the practice of this invention should incorporate sufficient basicity to remove residual ions in the nitrogen-containing organosilane and oxygen-containing organosilane product and effect stabilization of the resulting nitrogen-containing organosilane and oxygen-containing organosilane product. On the other hand, the basicity should be sufficiently weak in order to avoid reaction with the nitrogen-containing organosilane. Typically, the preferred pH of the medium using the weakly basic ion exchange resins will be from 7 to 8 during the contact period as per manufacturer's recommendations.

The weakly basic ion exchange resins preferably have amino functionality in the resin and preferably a tertiary amine group attached through a carbon atom to the resin structure. Preferably all of the resin is composed of carbon and hydrogen and nitrogen atoms. Anion impurities in the resin are to be avoided. Particularly preferred ion exchange resins are those made by the copolymerization of a monoolefinically unsaturated (halogenated or non-halogenated) hydrocarbon; a monoolefinically unsaturated heteroamine; a polyolefinically unsaturated hydrocarbon; or a polyolefinically unsaturated heteroamine. Illustrative of such monoolefinically unsaturated compounds are, for example, styrene, 4-chlorostyrene, 3-chlorostyrene, vinyltoluene, 4-chloromethylstryreme, vinylnaphthalene, vinylpyridine, 2-methyl-5-vinyl-pyridine, 2, 3-dimethyl-5-vinylpyridine, 2-methyl-3-ethyl-5-vinylpyridine, 2-methyl-5-vinylquinoline, 4-methyl-4-vinylquinoline, 1-methyl- or 3-methyl-5-vinylisoquinoline, and the like.

The polyolefinically unsaturated compounds may be, for example, one of the following: 1,4-divinylbenzene, divinylpyridine, divinyltoluenes, divinylnaphthalenes, trivinylbenzene, trivinylnaphthalenes, and the polyvinylanthracenes.

Amine functional ion exchange resins are available generally in two forms. One form is called a gel type resin and represents a standard type exchanger. The other form is called a macroreticular type anion exchange resin. In solid form they are easily separated from liquids such as BTBAS and DEAS by filtration. Illustrative of a commercial macroreticular tertiary amine weakly basic anion exchange resin is Amberlyst A-21, a trademark owned by, and which resin is produced by, Rohm and Haas Company, Philadelphia, Pa., or DOWEX Marathon WBA, a trademark owned by, and which resin is produced by, Dow Chemical Company, Midland, Mich. Illustrative of a commercial gel amine ion exchange resin is Amberlyst A-24, a trademark owned by, and which resin is produced by, Rohm and Haas Company, Philadelphia, Pa. It is a crosslinked acrylic gel structure with tertiary amine functional groups. Undesirable for this process is a strong base anionic macroreticular polymeric resin with terminal hydroxide groups as it may effect hydrolysis of some of the organosilanes causing significant product loss.

Other elements of the process for effecting stabilization of the nitrogen-containing organosilane and oxygen-containing organosilane product are contact temperature and residence time in which the resin and the nitrogen-containing organosilane and oxygen-containing organosilane materials remain in contact. Contact of the nitrogen-containing organosilane and organosilane normally is done at temperatures near room temperature to avoid thermal decomposition. Often the residence time is from 1 to 24 hours. Sometimes extended treatment of the product with the ion exchange resin can cause some decomposition so it is preferred to contact for a time sufficient to stabilize the nitrogen-containing organosilane and oxygen-containing organosilane without causing undo decomposition and then removing the product from contact with the resin.

It is recommended for the production of high purity, commercial grade nitrogen-containing and oxygen-containing organosilanes the treated ion exchange product be redistilled.

The following examples are intended to illustrate various embodiments of the invention and are not intended to restrict the scope thereof.

COMPARATIVE EXAMPLE 1

Study to Determine if Cl⁻ Causes Instability in BTBAS

In this study analysis of $Cl^-$ was made of stable and unstable BTBAS samples in an effort to determine if residual chloride levels remaining after distillation of BTBAS in product purification was the cause of BTBAS instability. Typical $Cl^-$ levels in BTBAS, as determined by ion chromatography, after distillation range from less than 10 ppm with most lots having between 1-3 ppm.

Close examination of the chloride levels in the unstable batches did not establish $Cl^-$ as the sole causative factor. Some lots with very low $Cl^-$ levels were unstable and yet some lots having high chloride levels were very stable. It was concluded some other factor was causing instability of BTBAS.

COMPARATIVE EXAMPLE 2

Study to Determine Effect of Acidic Compounds In Causing Decomposition of BTBAS

The purpose of this example was to determine if one could induce instability in BTBAS and increase the rate of decomposition of BTBAS through the introduction of small amounts of acidic compounds. It was believed this test might provide an insight as to the cause of excessive instability.

Experiment: In this example, a stable lot of BTBAS was divided into two portions, one sample being a reference standard and the other being exposed to approximately 1000 ppm of a few common anions. The exposure experiments were carried out inside a dry box. Six milliliters of BTBAS was transferred into an 8 ml vial and the anion source added. The vial was then capped, and agitated for several minutes and then allowed to settle overnight. The next day the Day 1 samples were run for assay. Five days later, the samples were run again and the rate of change of the main products and chromatographic differences were monitored. Then, the reference standard and exposed sample were compared in order to determine the rate of decomposition.

The anion sources were: Ammonium Sulfate, Sodium Sulfate, Sodium Sulfite, Ammonium Bicarbonate, Sodium Carbonate, Ammonium Chloride, and Sodium Nitrate.

Summary: The results show that the BTBAS reference which is stable became unstable when exposed to 1000 ppm of the above anions. The specific results are shown below:

Ammonium sulfate generated 2500 ppm S-2 after 1 day. After 5 days, the S-2 level was a 4850 ppm (461 ppm S-2 change per day from day 1 to 5). An unidentified peak was also formed at around 2200 ppm and that remained stable over the testing period, but was present at only 13 ppm in the control BTBAS.

Ammonium bicarbonate caused extreme decomposition of the BTBAS. At one day BTBAS assay was only 80% and at day 5 the BTBAS became a solid.

Ammonium chloride produced 900 ppm S-2 by day 1 and reached 2500 ppm on day 5. The unidentified peak seen also with Ammonium Sulfate was around 1100 ppm.

Sodium nitrate formed S-2 only, generating 1400 ppm on day 1 and 7250 ppm by day 5 (1165 ppm S-2 per day).

Sodium sulfate exposure also caused rapid generation of S-2 without adding new peaks. The level was about 1500 ppm on day 1 and 7200 ppm on day 5.

Sodium sulfite exposure had the least effect on the stability of the reference standard compared to the other anions. At Day 1, the S-2 level was 151 ppm and on Day 5, 1100 ppm. This was a rate of change of 196 ppm per day S-2. Uncharacteristically, the reference standard control showed a decomposition of 6 ppm per day S-2 increase from Day 1 to Day 5.

Ammonium chloride caused the least amount of decomposition to the test standard, generating an S-2 change of 300 ppm per day. Sodium carbonate had a delayed reaction with the BTBAS, on day 1 the S-2 level was only 89 ppm, the same of the control, but by day 5 had generated 7250 ppm.

In conclusion, all anions generated a significant S-2 change and caused the known stable reference standard to behave in an unstable manor, generating significant S-2.

COMPARATIVE EXAMPLE 3

Effect of Radical Scavenger Addition on Stability of BTBAS

The purpose of this example was to determine if there were free radicals in BTBAS samples and if the presence of those free radicals contributed in any way to the decomposition of unstable BTBAS. The procedure of Example 2 was followed except that the free radical scavengers, triethylamine, lithium amide and butylated hydroxytoluene (BHT) were added to samples of stable BTBAS and to unstable sample of BTBAS having a decomposition rate of around 100 ppm/day S-2 formation.

The exposure experiments were carried out inside a dry box. Six milliliters of BTBAS was transferred into an 8 ml vial and the scavenger source added at approximately 1000 ppm for the two solids and 0.5 ml for triethylamine. The vial was then capped, and agitated for several minutes and then allowed to settle overnight. The next day the day 1 samples were run for assay. Four days later, the samples were run again and the rate of change of the main products and chromatographic differences were monitored.

Summary: The known stable BTBAS samples exposed to these scavengers showed varying rates of decomposition. The control BTBAS reference standard showed no significant change over the test with triethylamine. The standard with BHT showed moderate decomposition, forming 3.4 ppm per day S-2. BHT caused a more significant disiloxane increase at a rate of 16 ppm/day. It was believed this increase in disiloxane was due to the fact that BHT has a sterically hindered hydroxyl group, and it was believed that BHT may be hydrolyzing BTBAS into the disiloxane through a nucleophilic attack of the oxygen lone pair to form a hydroxyl intermediate and then cleaving a t-butyl group to form a siloxane. It is also possible that the BHT became slightly hydrated and that free moisture caused the decomposition. BHT exposure also generated significant change in tertiary butyl amine (TBA), at a rate of 200 ppm/day which supports that the BHT was primarily reacting with the BTBAS and that it's effect on free radicals was unable to be determined.

Lithium amide had the least effect on the BTBAS reference standard although it made the stable material slightly more unstable, with a generation of S-2 of 3.5 ppm/day as compared to less than 1 ppm/day for the untreated reference sample.

Triethylamine showed a moderate stabilizing effect to unstable BTBAS. Triethylamine can form a fully alkylated ammonium derivative $(R_4N)^+X^-$ species. S-2 formation was reduced from the untreated unstable sample by a 30% improvement. BHT reduced overall BTBAS assay with significant formation of disiloxane. Lithium amide had little stabilizing effect, maintaining a 100 ppm S-2 per day decomposition rate.

Overall, the scavengers did not help to reduce BTBAS decomposition and some, primarily BHT, caused significant product loss. Although some stabilizing effects might be seen if studied over a longer time period, it was concluded something else was causing the nitrogen-containing organosilane to decompose and, based upon the results of Example 2, the presence of trace amounts of anions was deemed the likely cause.

EXAMPLE 4

Use of Ion Exchange Column to Treat BTBAS

The procedure of Example 2 was repeated except that the BTBAS was contacted with Amberlyst A-21 ion exchange resin manufactured by Rohm and Haas. The resin is a weakly basic macro-reticular resin with tertiary amine functionality. The Amberlyst A-21 resin was initially washed with greater than 10 volume equivalents of double de-ionized (DI) water (@18.2 Ω/cm) and then dried under vacuum and temperature for three days. If contaminating anions are present, it is believed the resins will remove anions pursuant to following equation:

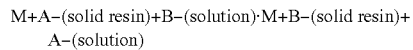

where A and B are the counter ions and M+ is the insoluble fixed cationic complement.

The first ion exchange column treatments were started. BTBAS samples were gravity fed through the ion exchange column bed at the rate of 4 bed volumes per hour. Material was passed through only once. The pH will remain within the range of 7 to 8 unless BTBAS becomes hydrolyzed.

The results showed essentially no improvement in stability. It was believed that perhaps the contact time was not enough to improve stability and maybe improved results might be seen with extended exposure times.

EXAMPLE 5

Effect of Weakly Basic Macroreticular Resin Extended Treatment on BTBAS Stability The procedure of Example 3 was repeated except that the BTBAS was contacted with Amberlyst A-21 ion exchange resin over an extended period of time. In carrying out the test, one sample set of extremely stable BTBAS and one sample set of extremely unstable BTBAS samples were soaked with dried A21 resin for 24 hours and then the BTBAS decanted off the resin. In another set, the samples remained in continuous contact with the resin for 41 days which constituted this test.

Results were compared against untreated samples for both the stable and unstable materials. The unstable BTBAS blank or untreated sample formed S-2 at a rate of 20.1 ppm per day. The BTBAS sample bulk soak with Amberlyst A-21 resin for 41 days generated 9.9 ppm per day of S-2 and thus decreased the decomposition of BTBAS by 50%. The BTBAS sample exposed to Amberlyst A-21 for a 24 hour exposure generated the most stable BTBAS product with an S-2 formation rate of 5.6 ppm per day. That reduction is an improvement of 72.2% over the untreated BTBAS sample over 41 days.

Summary: Exposure to Amberlyst A-21 induced moderate instability with regard to S-2 formation in the stable reference standard (1.8 ppm in the blank vs. 6.8 ppm in the soak and 8.9 ppm in the 24 hour exposure). In normally unstable BTBAS, the Amberlyst A-21 exposure reduced instability. The control blank formed S-2 at a rate of 20.1 ppm per day. The bulk soak generated 9.9 ppm per day S-2, a rate of 50% increased stability. The 24 hour exposure generated the most stable BTBAS with a S-2 formation rate of 5.58 ppm per day or a 72.24% increase in stability over the 41 days. In conclusion, treatment of unstable BTBAS with Amberlyst A-21 ion exchange resin seems to reduce S-2 formation and increase BTBAS stability.

EXAMPLE 6

Effect of Weakly Basic Macroreticular Resin Extended Treatment on BTBAS Stability Over 58 Days The procedure of Example 5 was followed except that stability was measured over a 58 day testing period and treatment was effected over different time periods. Two batches of BTBAS were studied, one with normal stability (1.3 ppm S-2 formation per day) and the other being moderately unstable (11 ppm S-2 per day).

In one set of runs the contact time of the BTBAS samples with Amberlyst A-21 resin was 3 hours of soaking and in another set runs the samples remained in constant contact with the A21 resin over the 58 days of the experimental run. These runs were compared with control samples where the stable and unstable BTBAS samples remained untreated.

The three hour contact of unstable BTBAS reduced the S-2 formation from 11 to 2.2 ppm per day. The bulk soak of BTBAS of the unstable BTBAS dropped S-2 formation from 11 down to 9.4 ppm per day.

The normal stability BTBAS material showed some instability when continuously exposed to the resin with S2 formation increasing from 1.3 to 3.5 ppm per day, but contacting BTBAS with Amberlyst A-21 for 3 hours reduced S-2 generation from 1.3 to 0.5 ppm per day.

In conclusion, the results show that BTBAS, whether normally stable or unstable, can be improved in stability by short term exposure and treatment with a weakly basic ion exchange resin. Compared against the extended contact times shown in Examples 5 and 6, the results showed that a 3 hour exposure of BTBAS was sufficient to complete the exchange of the counter ions and these samples showed the greatest improvement in overall stability.

EXAMPLE 7

Treatment of DEAS With Weak Acid Addition

The procedure of Example 5 was followed except diethylaminosilane was substituted for BTBAS. Unlike BTBAS, DEAS is extremely unstable with typical decomposition rates of 100 to 200 ppm per day.

Over time the Amberlyst A-21 ion exchange resin treated material was more stable than the untreated material even with the initial reduction in treated material purity. DEAS was only in contact with the resin as a bulk soak for 1 hour. Based upon the results from Examples 3 to 6, it is believed the stability of DEAS could be improved if a longer contact time had been employed. One other problem with this experiment was that the Amberlyst A-21 treated material suffered a 1% assay decrease probably due to inadequate drying, driving the reaction to form disiloxanes.

EXAMPLE 8

Treatment of Diethoxymethylsilane With Amberlyst A-21

In this example the procedure of Example 5 is repeated except that Diethoxymethylsilane (DEMS) is contacted with Amberlyst A-21 ion exchange resin. Stability is monitored over an extended period of time. It is found that treatment with Amberlyst A-21 can improve stability of the DEMS.

In conclusion, it is believed the treatment of nitrogen-containing silanes and oxygen-containing organosilanes with a weakly basic ion exchange resin can retard decomposition by scavenging residual ions or acids in the nitrogen-containing organosilane and oxygen-containing organosilane that can attack the nitrogen-containing organosilane and oxygen-containing organosilane molecules.

The invention claimed is:

1. A process for effecting stabilization of an organosilane selected from the group consisting of a nitrogen-containing organosilane having at least one N—H or Si—H or both and no pendant halogen atoms and an oxygen-containing organosilane having at least one Si—H comprised of the steps:
   (a) contacting the organosilane with a weakly basic ion exchange resin;
   (b) separating the organosilane from said weakly basic ion exchange resin; and
   (c) distilling said organosilane.

2. The process of claim 1 wherein the weakly basic ion exchange resin is exchanged with amine functionality.

3. The process of claim 2 wherein the organosilane is a nitrogen-containing organosilane is formed by the reaction of a chlorosilane and an organoamine.

4. The process of claim 1 wherein the organosilane is a nitrogen-containing silane represented by the formula:

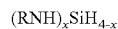      1 or

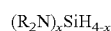      2 wherein R is $C_1$-$C_{10}$ an alkyl group, a cycloaliphatic group, or combined into a cyclic group and x=1, 2, or 3.

5. The process of claim 4 wherein the nitrogen-containing organosilane is selected from the group consisting of bis(tertiary-butylamino)silane diethylaminosilane and di-isopropylaminosilane.

6. The process of claim 5 wherein the nitrogen-containing organosilane has been purified by distillation prior to contact with the ion exchange resin.

7. The process of claim 5 wherein the residence time in which the ion exchange resin is in contact with the nitrogen-containing silane is from 1 to 50 hours.

8. The process of claim 7 wherein the contact time is from 3 to 24 hours.

9. The process of claim 5 wherein the amino functionality in the ion exchange resin is tertiary amine.

10. The process of claim 9 wherein the ion exchange resin is a macroreticular tertiary amine weakly basic anion exchange resin.

11. The process of claim 1 wherein said organosilane is an oxygen-containing organosilane represented by the formula:

$$(R^1O)_x SiH_{4-x} \qquad 1$$

or $$(R^1O)_x R^2_y SiH_{4-x-y} \qquad 2$$

wherein $R^1$ and $R^2$ are selected from $C_1$-$C_{10}$ alkyl groups, cycloaliphatic, or combined into a cyclic group and x=1, 2, 3 in formula 1 and x+y<4 in formula 2.

12. The process of claim 11 wherein the organosilane is diethoxymethyl silane and represented by formula 2 wherein $R^1$ is ethyl and $R^2$ is methyl which comprises:

(a) contacting the diethoxymethyl silane with a weakly basic ion exchange resin; and, (b) separating the diethoxymethyl silane from said weakly basic ion exchange resin.

13. The process of claim 12 wherein the ion exchange resin is a macroreticular tertiary amine weakly basic anion exchange resin.

14. A process for stabilizing an unstable batch of organosilane selected from the group consisting of bis(tertiary-butylamino)silane, diethylaminosilane (DEAS) and di-isopropylaminosilane having a decomposition rate of at least 50 ppm/day which comprises:

contacting said organosilane with a solid phase, weakly basic ion exchange resin;

separating said organosilane from said weakly basic ion exchange resin; and then, distilling said organosilane.

15. The process of claim 14 wherein said ion exchange resin is a macroreticular tertiary amine weakly basic anion exchange resin.

* * * * *